United States Patent [19]

Wang et al.

[11] Patent Number: 5,340,912

[45] Date of Patent: Aug. 23, 1994

[54] CYANATE RESINS

[75] Inventors: Pen-Chung Wang, Houston; Donald R. Kelsey, Fulshear, both of Tex.

[73] Assignee: Shell Oil Company, Houston, Tex.

[21] Appl. No.: 23,428

[22] Filed: Feb. 23, 1993

[51] Int. Cl.$^5$ .................. C08G 73/10; C08G 73/00; C07C 261/02

[52] U.S. Cl. .................. 528/322; 528/422; 560/301

[58] Field of Search .............. 528/322, 422; 560/301

[56] References Cited

U.S. PATENT DOCUMENTS 4,094,852  6/1978  Sundermann et al. ............ 524/710

Primary Examiner—John Kight, III
Assistant Examiner—Terressa Mosley

[57] ABSTRACT

A cyanate-functional compound is provided which can be described by the formula

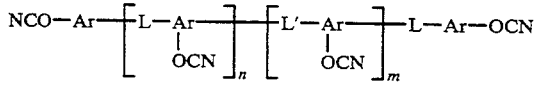

in which Ar is a $C_{6-20}$ aromatic moiety, L is a hexanenorbornane linking moiety, L' is a divalent cycloaliphatic moiety, and each of m and n is a number within the range of 0 to about 10. Such cyanate esters include the product of cyanation of the addition reaction of a phenol with a cyclohexene norbornene compound such as 5-(3-cyclohexen-1-yl)bicyclo[2.2.1]hept-2-ene. The resulting cyanate esters have low melt viscosity and low water absorbance in the cured state and are useful as the resinous component of high-performance electrical laminating and encapsulation formulations.

9 Claims, No Drawings

CYANATE RESINS

BACKGROUND OF THE INVENTION

This invention relates to novel thermosettable cyanate ester resins and to triazines derived therefrom.

Cyanate esters are a class of thermosettable materials of interest in electronics applications because of their ease of processing, low dielectric constant and high glass transition temperature. Aromatic cyanate esters comprising dicyclopentadiene linking moieties are known to cure to triazine resins having high Tg and low moisture absorbance. For high-performance electronic applications, thermosettable resins having increasingly low melt viscosity (for ease and speed of processing) and low water absorbance in the cured state are required.

It is therefore an object of the invention to provide novel cyanate esters having low melt viscosity and low water absorbance in the cured state.

SUMMARY OF THE INVENTION

According to the invention, a cyanate-functional compound is provided which can be described by the formula

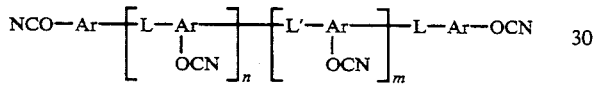

in which Ar is a $C_{6-20}$ aromatic moiety, L is a cyclohexanenorbornane linking moiety, L' is a divalent cycloaliphatic moiety, and each of m and n is a number within the range of 0 to about 10. Such cyanate esters include the product of cyanation of the addition reaction of a phenol and a cyclohexene-norbornene compound such as 5-(3-cyclohexen-1-yl)-bicyclo[2.2.1]hept-2-ene. Such cyanate esters are useful as the resinous component of electrical laminating and encapsulation formulations.

DETAILED DESCRIPTION OF THE INVENTION

The invention cyanate esters can be prepared by reacting the precursor polyphenols (described below) with a cyanogen halide such as cyanogen chloride or cyanogen bromide in the presence of a basic catalyst. The reaction can be carried out at a temperature within the range of about −15° C. to about 60° C., preferably about 0° to about 20° C. Suitable catalysts include alkali metal hydroxides such as sodium hydroxide or potassium hydroxide; alkali metal alkylates such as sodium methylate or potassium methylate; and tertiary amines such as trimethyl amine, triethyl amine, methyl diethyl amine, tripropyl amine, tributyl amine, dimethyl cyclohexyl amine and diethyl aniline. The preferred basic catalyst is triethylamine. The basic catalyst is generally present in the reaction mixture in an amount of at least about 1 mole, preferably about 0.8 to about 1.2 moles, per mole of the cyanogen halide. The cyanogen halide is generally present in an amount within the range of about 0.8 to about 1.5 moles per phenolic hydroxyl group.

The precursor polyphenols can be described by the formula

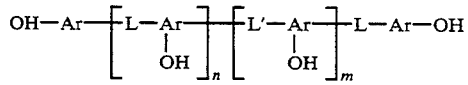

in which Ar is a $C_{6-20}$ aromatic moiety, L is a divalent cyclohexanenorbornane moiety, L' is a divalent cycloaliphatic moiety, and each of m and n is a number within the range of 0 to about 10. Such polyphenols can be prepared by the addition reaction of a phenol with a cyclohexenenorbornene compound such as 5-(3-cyclohexen-1-yl)bicyclo[2.2.1]hept-2-ene (herein referred to as the "cyclohexenenorbornene" compound). Suitable phenols include mono- and polynuclear phenols having at least one unsubstituted position ortho- or para- to a phenolic hydroxyl group, such as phenol, cresol, 3,4- and 3,5-dimethylphenol, resorcinol, biphenol, 1-naphthol and bisphenol A or F. Phenol is preferred.

Suitable cyclohexenenorbornene compounds include

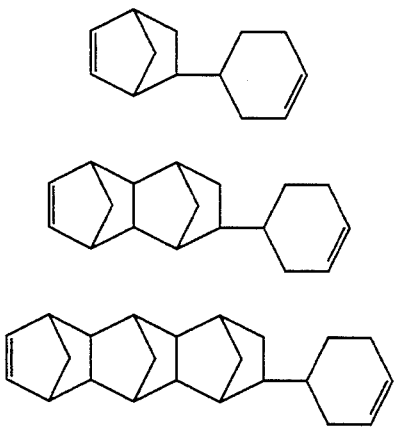

referred to herein as "monoadduct," "diadduct" and "triadduct," respectively, and isomers thereof.

The starting phenol can also include a derivative L' of a cycloaliphatic diene such as dicyclopentadiene, cyclopentadiene, norbornadiene dimer, norbornadiene, methylcyclopentadiene dimer, limonene, 1,3- and 1,5-cyclooctadiene, α- and γ-terpinene, 5-vinylnorbornene, 5-(3-propenyl)-2-norbornene, and cyclopentadiene oligomers for example. The preparation of such a phenol is illustrated in Example 6 herein.

The cyclohexenenorbornene starting material is an addition product of 4-vinylcyclohexene and cyclopentadiene which can be prepared by contacting 4-vinylcyclohexene and dicyclopentadiene, preferably in the presence of a polymerization inhibitor such as t-butyl catechol, at a temperature of at least about 150° C., preferably about 180° C. to 260° C., for a time within the range of about 2 hours to about 8 hours. Under these conditions, the dicyclopentadiene is cracked to cyclopentadiene, and the vinylcyclohexene and cyclopentadiene undergo an addition reaction to produce a mixture of mono-, di- and poly-adducts as well as cyclopentadiene oligomers (e.g., trimer, tetramer, pentamer, etc.). For recovery of one or more desired compounds, the reaction product mixture containing predominantly 5-(3-cyclohexen-1-yl)bicyclo[2.2.1]hept-2-ene (monoadduct) is allowed to cool to about 50°–70° C. and is stirred under reduced pressure to strip off unreacted vinylcyclohexene. The reaction product is then purified by fractional vacuum distillation for removal of by-products including, optionally, di- and polyadducts, and the purified product is passed through an adsorbent bed for removal of t-butyl catechol. Preparation of a vinylcyclohexene/cyclopentadiene adduct is illustrated in Example 1 herein.

The phenolic precursors of the invention cyanate esters can be prepared by contacting, under addition reaction conditions, the above-described vinylcyclohexene/cyclopentadiene adduct with a molar excess, preferably about 10 to about 30 moles, of the selected phenol per mole of the adduct. The reaction is most efficiently carried out in the presence of a Lewis acid such as $BF_3$, coordination complexes thereof such as boron trifluoride etherate, $AlCl_3$, $FeCl_3$, $SnCl_4$, $ZnCl_2$, silica and silica-alumina complexes and at an elevated temperature within the range of about 70° to about 200° C., preferably about 100° to about 180° C. The reaction is continued until the desired degree of reaction has been completed, usually for a time within the range of about 30 minutes to about 10 hours, preferably about 1 hour to about 3 hours. Preparation of such polyphenols is illustrated in Examples 2, 4 and 6 herein. Cyanation of the resulting polyphenols to prepare the invention cyanate esters is described above and in Examples 3, 5 and 7 herein.

The invention cyanate-functional compounds are cured by exposure to elevated temperature of at least 150° C., generally within the range of about 150° to about 250° C., for a time which can vary widely depending upon the cure schedule and the thickness of the part, generally greater than about 0.25 hour. Optimum properties in the cured resin can be achieved by a staged heating process employing higher temperature in each stage, as illustrated in the Examples below. The cyanate esters can be co-cured with other cyanate ester compounds and/or with other thermosettable resins such as bismaleimide resins and epoxy resins.

The invention cyanate esters are useful in preparing electrical laminates and in molding compounds.

EXAMPLE 1

Preparation of 5-(3-cyclohexen-1-yl)bicyclo[2.2.1]hept-2-ene

Dicyclopentadiene and 4-vinylcyclohexene in equimolar mixture were heated in an autoclave at 240° C. for 4-4.5 hours. The reaction product was diluted with cyclohexane and passed through a packed bed of alumina to remove the t-butylcatechol inhibitor introduced with the reactants. The resulting product mixture was distilled in a wiped film evaporator at 3 mm Hg pressure at 90° C. to produce a light fraction containing unreacted vinylcyclohexene and dicyclopentadiene and the mono-adducts of 4-vinylcyclohexene and cyclopentadiene. A 150 g sample of this distillate was vacuum distilled using a 10-tray Oldershaw column to give four fractions. The fourth fraction, 65 g, was shown by gas chromatographic analysis to consist of 0.15% dicyclopentadiene, 88.3% endo-5-(3-cyclohexen-1-yl)-2-norbornene, 6.1% exo-5-(3-cyclohexen-1-yl)-2-norbornene and two additional components present in the amount of 1.9% and 2.4% which are believed to be isomeric adducts of the formula

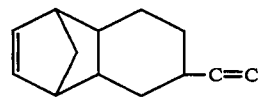

several additional components totalling about 0.4%, 0.4% tricyclopentadiene and about 0.4% unidentified components. Analysis of the fraction by nuclear magnetic resonance indicated about 87 mole percent of the endo adduct, about 9 mole percent of the exo adduct and about 5% of the isomeric adducts.

EXAMPLE 2

Preparation of Precursor Polyphenol A.

To a reactor equipped with a stirrer, condensor and addition funnel were added 188.2 g (2.0 mole) of phenol and 1.0 g of $BF_3.Et_2O$ catalyst. The mixture was heated to 70° C. and 13.67 g of 5-(3-cyclohexen-1-yl)bicyclo[2.2.1]hept-2-ene was added over a 20-minute period. The temperature was raised to 150° C. over a 1½-hour period and was held for about 2½ hours. Unreacted phenol was distilled off. The recovered polyphenol had a terminal hydroxyl group concentration of 0.495 equivalent/100 g and a melting point of 70°–80° C.

EXAMPLE 3

Preparation and Curing of Cyanate Resin.

In 450 ml of chloroform were dissolved 20.65 g (0.195 mole) of cyanogen bromide and 33.55 g (0.195 mole) of polyphenol A derived from the addition reaction of phenol and 5-(3-cyclohexen-1-yl)bicyclo[2.2.1]hept-2-ene. The resulting solution was ice-cooled. Triethylamine (20.72g, 0.20 mole) was stirred into the solution over a period of 60 minutes, during which the reaction temperature was maintained at 5°–10° C. After the reaction was complete, the chloroform solution was washed several times with $H_2O$ and removed under reduced pressure to give 31.86 g of an amber viscous liquid. IR analysis of the product gave a characteristic absorption band of a cyanic acid ester group at 2250 cm$^{-1}$. The product can be represented structurally as

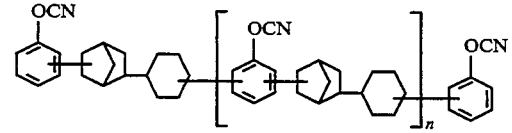

The cyanate acid ester was cured at 200° C. for 2 hours, 220° C. for 2 hours, and 240° C. for 4 hours to provide a cured product having a Tg of 190° C., heat decomposition temperature of 450° C. and water gain of 1.0% (2 weeks 93° C.). Mechanical and electrical properties are shown in Table 1.

EXAMPLE 4

Preparation of Polyphenol Precursor B

To a reactor equipped with a stirrer, condensor and addition funnel were added 376 g (4.0 mole) of phenol and 2.0 g of $BF_3.Et_2O$. The reaction mixture was heated to 70° C., and 48 g (0.2 mole) of diadduct was added over a 20-minute period. The temperature was raised to 150° C. over a 1½-hour period and held for about 2½ hours. Unreacted phenol was distilled. The recovered product melted over the range of 85°–95° C. and had a phenolic hydroxyl content of 0.47 eq/100 g.

EXAMPLE 5

Preparation and Cure of Cyanate Resin

The procedure described in Example 3 was repeated starting with 50.0 g of polyphenol B, 24.91 g (0.235 mole) cyanogen bromide and 23.78 g (0.235 mole) of triethylamine. 57.7 g of a glassy solid having a melting point of 45°–55° C. was isolated. The product can be represented structurally as

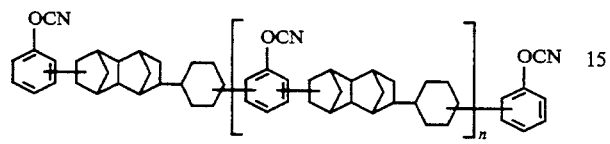

The product was cured by heating at 200° C. for 2 hours, 220° C. for 2 hours and 240° C. for 4 hours to provide a cured solid having a Tg of 221° C., a heat decomposition temperature of 450° C. and water gain of 1.02% (2 weeks 93° C.). Mechanical and electrical properties are shown in Table 1.

EXAMPLE 6

Preparation of Precursor Polyphenol C

To a reactor equipped with a stirrer, condensor and addition funnel, 295.7 g (3.14 mole) of phenol and 2.0 g of BF$_3$.Et$_2$O were added. The mixture was heated to 70° C., and 13.67 g (0.07856 mole) of 5-(3-cyclohexen-1-yl) bicyclo[2.2.1]hept-2-ene and 10.29 g (0.07856 mole) of dicyclopentadiene were added over a 20-minute period. The temperature was raised to 150° C. over a 1½-hour time period and was held for 2½ hours. Unreacted phenol was distilled off. The recovered polyphenol melted over the range of 70°–78° C.

EXAMPLE 7

Preparation and Cure of Cyanate Resin

The procedure described in Example 3 was repeated starting with 50.03 g (0.291 mole) of polyphenol C, 30.82 g (0.291 mole) of cyanogen bromide and 30.86 g (0.305 mole) of triethylamine. 59.4 g of cyanate resin was isolated as a heavy oil. The product includes the structural units

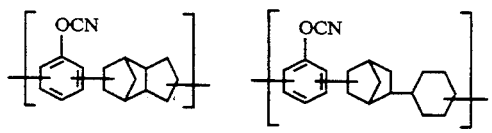

Curing of the product cyanate-functional material at 200° C. for 2 hours, 220° C. for 2 hours and 240° C. for 4 hours gave a cured product having a Tg of 180° C. and a heat decomposition temperature of 450° C.

EXAMPLE 8

Preparation of Precursor Polyphenol D (Comparison)

To a reactor equipped with a stirrer, condensor and addition funnel were added 188.2 g (2.0 mole) of phenol and 1.0 g of BF$_3$.Et$_2$O. The reaction mixture was heated to 70° C., and 13.2 g (0.1 mole) of dicyclopentadiene were added over a 20-minute period and held for 2½ hours. Unreacted phenol was distilled. The recovered product had a melting range of 115°–120° C. and a phenolic hydroxyl content of 0.62 eq/100 g.

EXAMPLE 9

Preparation and Cure of Cyanate Resin (Comparison)

The procedure described in Example 3 was repeated starting with 100 g (0.62 mole) of polyphenol D, 65.7 g (0.62 mole) of cyanogen bromide and 62.74 g (0.62 mole) of triethylamine. 93 g of cyanate resin was isolated as a semisolid. The product can be represented structurally as

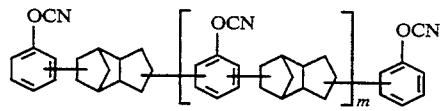

The product was cured by heating at 200° C. for 2 hours, at 220° C. for 2 hours and at 240° C. for 4 hours, to produce a product having a Tg of 218° C. (DSC) and 250° C. (DMA, Tan delta) and a heat decomposition temperature of 450° C. The mechanical and electrical properties are shown in Table 1 for comparison.

TABLE 1

| Neat Resin Properties of Cyanate Resins | | | |
|---|---|---|---|
|  | Ex. 3 | Ex. 5 | Ex. 9 |
| Tg (DSC) | 190 | 221 | 218 |
| Flexural properties (RT/Dry) | | | |
| Strength (ksi) | 13.4 | 10.7 | 16.9 |
| Modulus (ksi) | 540 | 508 | 532 |
| Elongation (%) | 2.5% | 2.11% | 3.2% |
| Flexural properties (Hot/Wet) | | | |
| Strength (ksi) | 8.0 | 5.34 | 8.9 |
| Modulus (ksi) | 440 | 477 | 485 |
| Elongation (%) | 1.9% | 1.00% | 1.86% |
| Modulus retention (%) | 82 | 94 | 91 |
| Fracture toughness (Kq) | 916 | 503 | 468 |
| Moisture gain (%) | 1.1% | 1.02% | 1.5% |
| Dielectric constant at 1 MHz | 2.65 | 2.73 | 2.89 |

Cure of Cyanate Resin with Bismaleimide Resin

The cyanate resin prepared in Example 3 (12.72 g) was melt-blended with Compimide ® MDAB bismaleimide (6.36 g) at 120°–130° C. The mixture was heated in an oven at 200° C. for 2 hours, at 220° C. for 2 hours and at 240° C. for 4 hours. The resulting cured product had a Tg of 182° C. and a heat decomposition temperature of 450° C.

EXAMPLE 10

Cure of Cyanate Resin with Bismaleimide Resin

The cyanate resin prepared in Example 5 (27.0 g) was melt-blended with Compimide ® MDAB bismaleimide (3 g) at 120°–130° C. The mixture was then heated in an oven at 200° C. for 2 hours, at 220° C. for 2 hours and at 240° C. for 4 hours. The resulting cured material had a Tg of 223° C., water gain of 1.29% (2 weeks, 93° C.) and dielectric constant of 2.81 at 1 mHz.

We claim:

1. A compound of the formula

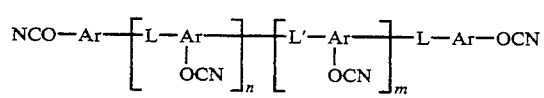

in which Ar is a $C_{6-20}$ aromatic moiety, L is a divalent cyclohexanenorbornane linking moiety, L' is a divalent cycloaliphatic linking moiety, and each of m and n is a number within the range of 0 to about 10.

2. The compound of claim 1 in which each Ar is phenyl.

3. The compound of claim 1 in which L is selected from the group consisting of

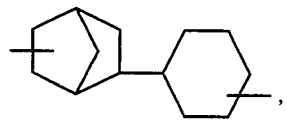

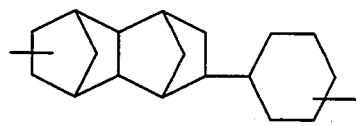

and

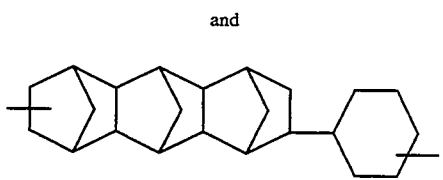

4. The compound of claim 1 in which L' is

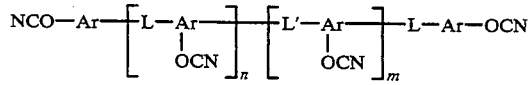

5. A compound of the formula

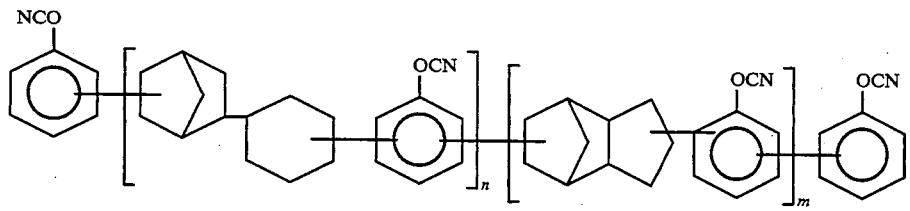

in which n is a number within the range of 0 to about 10.

6. The compound of claim 5 in which n is a number within the range of 0 to 1.

7. A compound of the formula

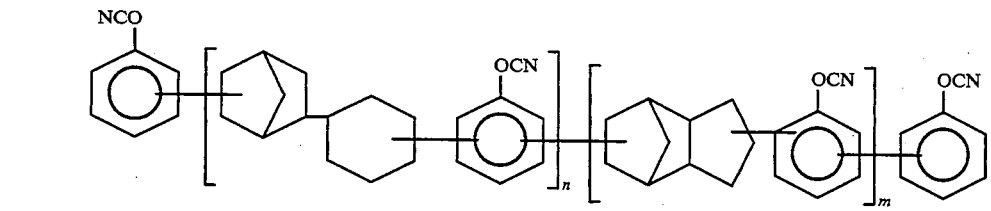

in which each of m and n is a number within the range of 0 to about 10.

8. The solid product of subjecting the composition of claim 1 to a temperature of at least about 150° C. for at least about 0.25 hour.

9. A composition comprising a bismaleimide and a compound of the formula

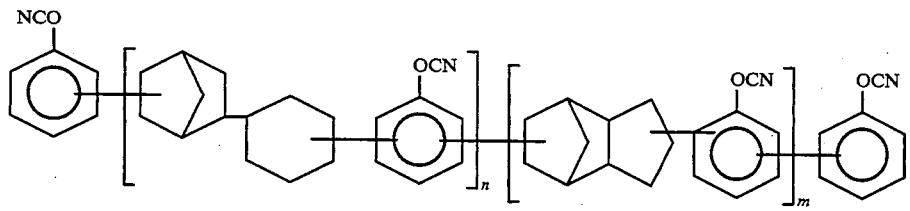

in which Ar is a $C_{6-20}$ aromatic moiety, L is a divalent cyclohexanenorbornane linking moiety, L' is a divalent cycloaliphatic linking moiety, and each of m and n is a number within the range of 0 to about 10.

* * * * *